Figure 1:
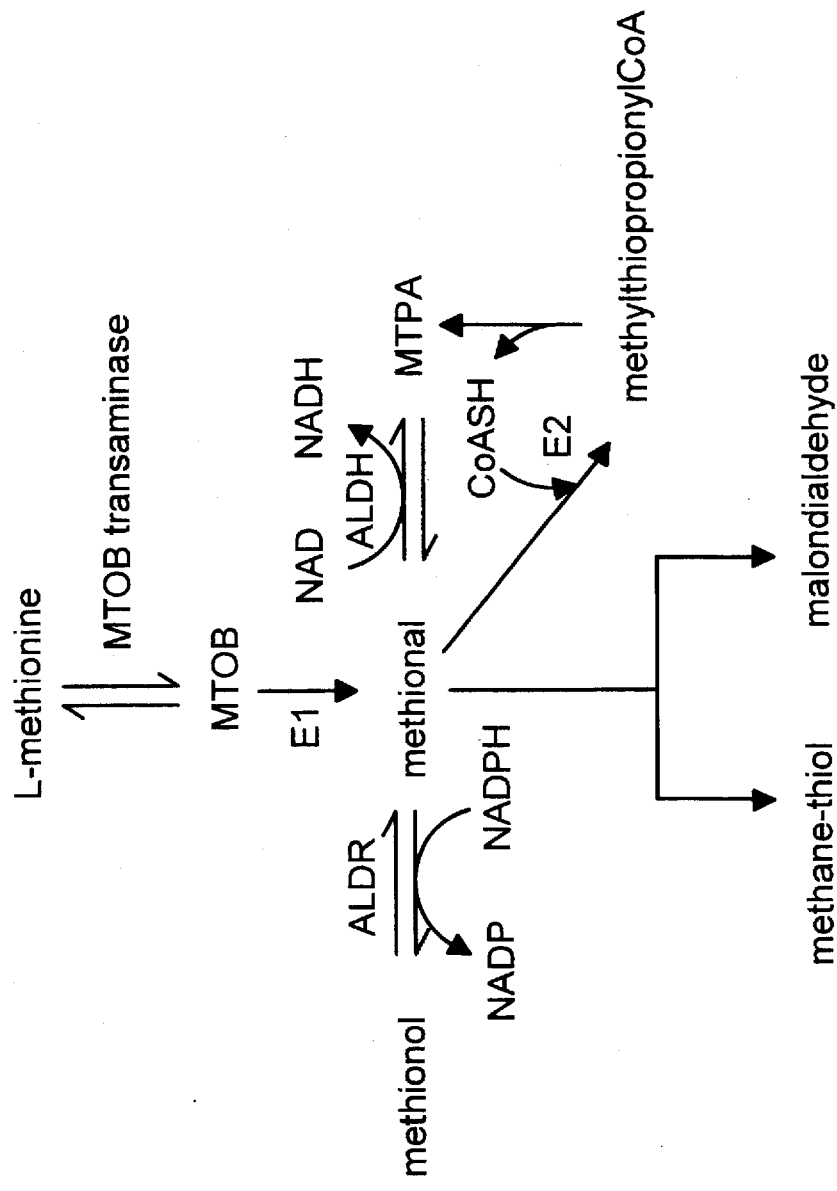

United States Patent [19]
Quash et al.

[11] Patent Number: 5,744,499
[45] Date of Patent: Apr. 28, 1998

[54] APOPTOSIS-MODULATING FACTORS INFLUENCING THE INTRACELLULAR CONCENTRATION OF METHIONAL/ MALONDIALDEHYDE

[75] Inventors: Gérard Anthony Quash, Francheville; Alain Doutheau, Lyons, both of France

[73] Assignee: Centre International de Recherches Dermatologiques Galderma, Valbonne, France

[21] Appl. No.: 579,244

[22] Filed: Dec. 28, 1995

[30] Foreign Application Priority Data

Dec. 29, 1994 [FR] France .................... 94 15884

[51] Int. Cl.$^6$ .................... A61K 31/15
[52] U.S. Cl. .................... 514/639; 514/89; 514/351; 514/458; 514/702
[58] Field of Search .................... 514/702, 639, 514/89, 351, 458

[56] References Cited

PUBLICATIONS

Biochem. J., vol. 305, No. pt. 3, 1995, pp. 1017–1025, G. Quash et al., "Methional derived from 4-methylthio-2-oxobutanoate is a cellular mediator of apopotosis in baf3 lymphoid cells."

Biochem. Pharmacol., vol. 45, No. 8, 1993, pp. 1631–1644, G. Ogier et al., "Contribution of 4-methylthio-2-oxobutanoate and its transaminase to the growth of methionine-dependent cells in culture: effect of transaminase inhibitors."

Chem. Biol. Interact., vol. 50, No. 1, 1984, pp. 87–96, F.W. Summerfield et al., "Cross-linking of DNA in liver and testes of rats fed 1,3-propanediol."

J. Neurobiol., vol. 24, No. 4, 1993, pp. 433–446, M.D. Linnik et al., "Induction of programmed cell death in a dorsal root ganglia X neuroblastoma cell line."

J. Neurosci., vol. 14, No. 7, 1994, pp. 4385–4392, R.R. Ratan et al., "Macromolecular synthesis inhibitors prevent oxidative stress-induced apoptosis in embryonic cortical neurons by shunting cysteine from protein synthesis to glutathione."

*Primary Examiner*—Amelia Owens
*Attorney, Agent, or Firm*—Burns, Doane, Swecker & Mathis, L.L.P.

[57] ABSTRACT

Apoptosis (programmed cell death) in mammalian organisms is modulated, whether initiated or suppressed, for example for preventing and/or combating photoinduced or chronologic aging of the skin or for treating a wide variety of human afflictions, by administering thereto, for such prolonged period of time as is required to elicit the desired response, an effective apoptosis-modulating amount of at least one active species selected from among methional, malondialdehyde, or factor influencing the intracellular concentration of methional or malondialdehyde.

48 Claims, 1 Drawing Sheet

APOPTOSIS-MODULATING FACTORS INFLUENCING THE INTRACELLULAR CONCENTRATION OF METHIONAL/MALONDIALDEHYDE

BACKGROUND OF THE INVENTION

1. Technical Field of the Invention

The present invention relates to the pharmaceutical application of methional, malondialdehyde, and any factor influencing the intracellular proportion or concentration of methional or malondialdehyde, and, more especially, relates to the use of the above active agents for modulating the phenomenon of programmed cell death (apoptosis).

This invention also relates to pharmaceutical or cosmetic compositions which modulate apoptosis, comprising an effective amount of an active species selected from among methional, malondialdehyde, and any factor influencing the intracellular proportion of methional or malondialdehyde, in a pharmaceutically or cosmetically acceptable vehicle, diluent or carrier therefor.

The present invention also relates to a regimen for preventing and/or combating photoinduced or chronological aging of the skin.

2. Description of the Prior Art

There are two known types of mechanisms involved in cell death. The first conventional type is termed necrosis. Morphologically, necrosis is characterized by a swelling of the mitochondria and cytoplasm and by changes in the cell nucleus, followed by destruction of the cell and the autolysis thereof, these phenomena being accompanied by inflammation. Necrosis occurs passively and episodically. Tissular necrosis is generally the result of physical cell trauma or chemical poisoning, for example.

The other form of cell death is termed apoptosis (J. F. R. Kerr and A. H. Wylie, Br. J. Cancer, 265, 239 (1972)). However, in contradistinction to necrosis, apoptosis does not produce inflammation. Apoptosis is described as occurring under various physiological conditions. It is a highly selective form of cellular suicide characterized by readily observable morphological and biochemical phenomena. Thus, condensation of chromatin is observed, whether or not accompanied by endonuclease activity, the formation of apoptic bodies, and fragmentation of desoxyribonucleic acid (DNA) caused by activation of endonucleases in DNA fragments consisting of 180–200 base pairs. These fragments can be rendered visible using agarose gel electrophoresis.

Apoptosis may be considered to be programmed cell death involved in the growth, differentiation, and homeostasis of tissue. It is considered, therefore, that cell differentiation, growth, and maturation are closely linked to apoptosis. Accordingly, a balance among all of these phenomena exists in healthy humans.

In the medical field, a number of pathological occurrences exhibit a modified, and even uncontrolled, apoptosis mechanism, or an apoptosis mechanism which does not trigger the disturbance of another biological phenomenon in order to attain balance. Thus, it is described in the literature that purposeful modulation of apoptodis entailing the initiation or suppression thereof may permit treatment of numerous diseases, and, more specifically, diseases associated with cellular hyperproliferation, such as cancer, autoimmune diseases, or allergies; or, to the contrary, diseases associated with cell disappearance, such as the immunodeficiency syndrome of the human immunodeficiency virus (HIV), neuro-degenerative conditions (e.g., Alzheimer's), or excessive damage caused by myocardial infarction or stroke.

More concretely, it has been observed in the field of oncology that numerous anti-cancer drugs, such as adriamycin and cyclophosphamide, can trigger apoptosis.

In the field of cosmetology, the signs of skin aging result basically from a malfunction of the principal biological skin mechanisms, which initiate, most notably, the apoptosis mechanism. It may thus be considered that any species capable of modulating apoptosis can also prevent and/or combat the appearance of aging and the existing signs of aging, such as wrinkles.

However, the link between species exogenous and endogenous to the cell and the cellular response triggering or suppressing apoptosis is to date unknown.

SUMMARY OF THE INVENTION

It has now unexpectedly been determined that apoptosis can be induced by increasing the intracellular concentration of a natural metabolite, i.e., methional (3-methylthiopropanal) or malondialdehyde. It has also now been determined that the in vivo transformation of methional into malondialdehyde can be deregulated by the expression of oncogenes, such as the gene bcl2. This bcl2 gene is described as being capable of inhibiting apoptosis triggered by reactive oxygenated substrates in neuronal cells. Kane et al, Science, 262, 1274–1277 (1993).

Briefly, the present invention features the pharmaceutical application of methional, malondialdehyde, and any factor influencing the intracellular proportion of methional or malondialdehyde, for modulating the phenomenon of programmed cell death.

The present invention also features pharmaceutical or cosmetic compositions comprising an effective apoptosis-modulating amount of an active agent selected from among methional, malondialdehyde, and any factor influencing the intracellular concentration of methional or malondialdehyde, in a pharmaceutically or cosmetically acceptable vehicle, carrier or diluent therefor.

DETAILED DESCRIPTION OF BEST MODE AND SPECIFIC/PREFERRED EMBODIMENTS OF THE INVENTION

More particularly according to the present invention, methional, malondialdehyde, and all factors influencing the intracellular proportion of methional can be used either singly or, preferably, in admixture. It will, of course, be appreciated that the selection of a particular active species depends on the goal to be attained, namely, either to induce apoptosis or to suppress same.

Thus, in a preferred embodiment of the invention, compositions triggering apoptosis comprise an effective amount of methional, malondialdehyde, or any factor which increases the intracellular proportion of methional or malondialdehyde, in combination with a pharmaceutically or cosmetically acceptable vehicle, diluent or carrier therefor.

In another embodiment of this invention, compositions for suppressing apoptosis comprise an effective amount of any factor which decreases the intracellular amount of methional or malondialdehyde, combined with a pharmaceutically or cosmetically acceptable vehicle, diluent or carrier therefor.

With particular respect to the metabolism of methional, it is known to this art that 4-methylthio-2-oxobutanoic acid can be metabolized in vivo by the branched-chain oxoacid dehydrogenase complex present in the mitochondria of liver, heart, and skeletal muscle cells by means of methional, to yield methylthiopropionylCoA [see G. Wu and S. J. Yeaman, *Biochem. J.*, 257, 281–284 (1969); D. Haussinger, T. Stehle and W. Gerok, *J. Biol. Chem.*, 366, 527–536 (1985); S. M. A. Jones and S. J. Yeaman, *Biochem. J.*, 237, 621–623 (1986)]. It too is known that 4-methylthio-2-oxobutanoic acid can be metabolized in vivo by transamination, thus forming methionine (see G. Ogier, J. Chantepie, C. Deshayes, B. Chantegrel, C. Chariot, A. Doutheau and G. Quash, *Biochem. Pharmacol.*, 45, 1631–1644 (1993)). Methional may also potentially be reduced or oxidized into methional employing an aldehyde reductase, or into methylthiopropionic acid, employing an aldehyde dehydrogenase. Methional in combination with the OH⁻ radical can, lastly, produce malondialdehyde and methanethiol by means of a β-hydroxylation reaction. Thus, to better describe methional, malondialdehyde, and the factors influencing the intracellular proportions thereof, the FIGURE of Drawings illustrates the metabolism of methional, without, however, limiting the scope of the present invention.

In said FIGURE of Drawing:

MTOB represents 4-methylthio-2-oxobutanoic acid;

MTPA represents methylthiopropionic acid;

E1 represents the decarboxylase of the branched-chain oxoacid dehydrogenase complex, whose cofactor is thiamine pyrophosphate (TPP);

E2 represents the transacylase of the branched-chain oxcacid dehydrogenase complex, whose cofactor is thioctic acid (TA);

ALDR represent the aldehyde reductase;

ALDH represents the aldehyde dehydrogenase.

According to the invention, by the expression "factor influencing the intracellular proportion (or concentration) of methional or malondialdehyde" are intended active compounds selected from among the precursors and species of methional and malondialdehyde and the inhibitors and activators of the enzymes involved in the metabolism of methional and malondialdehyde. It will, therefore, be readily appreciated, from the representation of the metabolism of methional and malondialdehyde shown in the FIGURE of Drawing, how these compounds, i.e., methional and malondialdehyde, when introduced into a cell system, can elicit the temporary or long-lived modification of the intracellular amount of methional or malondialdehyde.

The precursors and products of methional and malondialdehyde can be precursors and products of the intracellular metabolism of methional, such as 4-methylthio-2-oxobutanoic acid, methionine, methionol, methylthiopropionic acid, and methylthiopropionylCoA.

The precursors and products of methional and malondialdehyde can also be compounds which exhibit, in situ, the ability to release methional, malondialdehyde, or a factor influencing the intracellular proportion of methional and malondialdehyde, such as esters and thioesters of methional or malondialdehyde, which release in situ methional, malondialdehyde, or 4-methylthio-2-hydroxybutanoic acid, which will be metabolized in situ into 4-methylthio-2-oxobutanoic acid. In the pharmaceutical arts, these compounds are commonly termed "prodrugs."

In the event that apoptosis is to be induced, methional, malondialdehyde, or the precursors or products of methional or malondialdehyde are advantageously employed in combinatory immixture with the inhibitors of enzymes involved in metabolic methional-elimination reactions, other than the aforementioned β-hydroxylation reaction (which transforms methional into malondialdehyde), or in combinatory immixture with activators of β-hydroxylase, which is the enzyme involved in the transformation of methional into malondialdehyde. Thus, exemplary are combinatory immixtures of 4-methylthio-2-oxobutanoic acid with an inhibitor of the transaminase involved in the transformation of 4-methylthio-2-oxobutanoic acid into methionine, such as the inhibitors indicated above.

Also exemplary are combinatory immixtures of methional or a factor increasing the intracellular amount of methional with compounds which increase the free radical OH⁻ content. Accordingly, BCNU (N,N-bis(2-chloroethyl)-N-nitresourea) is representative, since it is a glutathione reductase inhibitor, thereby permitting increasing the intracellular proportions of reactive oxygenated species, such as the OH⁻ radical, which is one of the bases of the β-hydroxylation reaction producing malondialdehyde.

This combination is especially advantageous in pathologies characterized by an excess expression of the bcl2 gene. These pathologies include, in particular, breast cancer, B cell lymphoma, leukemia, neuroblastoma, adenocarcinoma of the prostate, prolactinoma, and other pituitary adenomas. The subject combination may thus elicit partial, and even total, inhibition of this drug-resistant characteristic.

Advantageously, at least one inhibitor of the transaminase involved in the transformation of 4-methylthio-2-oxobutanoic acid into methionine is included in the immixture, such as those described above, and, more especially, the compound corresponding to formula (9).

Among the inhibitors and activators of the enzymes involved in methional metabolism, exemplary are the inhibitors and activators of the branched-chain oxoacid dehydrogenase complex involved in the transformation of 4-methylthio-2-oxobutanoic acid into methylthiopropionylCoA, effected using methional; or the inhibitors and activators of the transaminase involved in the transformation of 4-methylthio-2-oxobutanoic acid into methionine; the inhibitors and activators of the aldehyde reductase responsible for reduction of methional into methionol or of the aldehyde dehydrogenase responsible for oxidation of methional to form methylthiopropionic acid; or the activators and inhibitors of β-hydroxylase, which is the enzyme involved in the transformation of methional into malondialdehyde.

Thus, a representative inhibitor of the branched-chain oxoacid dehydrogenase complex, and, hence, a representative factor decreasing the intracellular amount of methional or malondialdehyde, is 2-oxobutyrate, which is a well-known substrate of this complex (see S. M. A Jones and A. I. Cederbaum, *Arch. of Biochem. and Biophys.*, 199, 438–447 (1980)), as well as are ketoleucine, ketoisoleucine, and ketovaline, which are other substrates of this complex.

Exemplary inhibitors of the transaminase involved in the transformation of 4-methylthio-2-oxobutanoic acid into methionine, and thus, exemplary factors increasing the intracellular content of methional or malondialdehyde, are the materials described by G. Ogier, J. Chantepie, C. Deshayes, B. Chantegrel, C. Chariot, A. Doutheau and G. Quash, *Biochem. Pharmacol.*, 45, 1631–1644 (1993).

More especially, the inhibitors of the transaminase involved in the transformation of 4-methylthio-2-oxobutanoic acid into methionine are selected from among the compounds having the structural formulae (1) to (9) below:

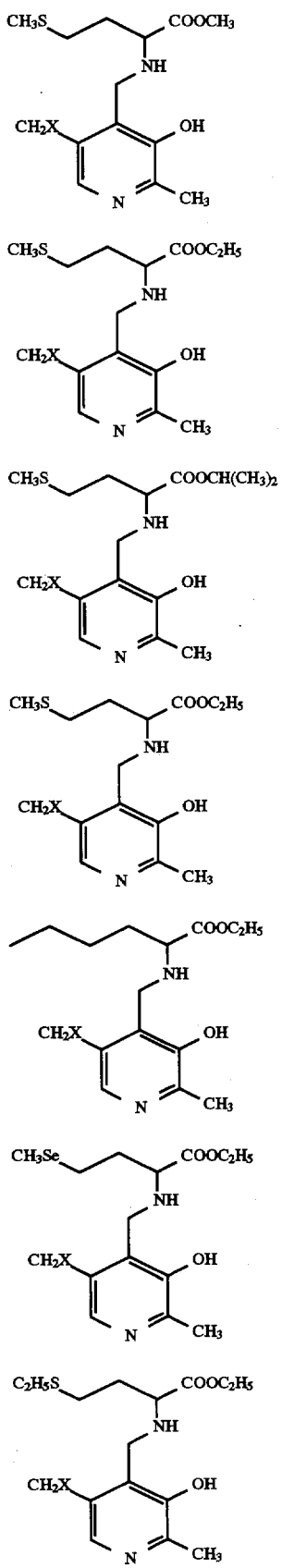

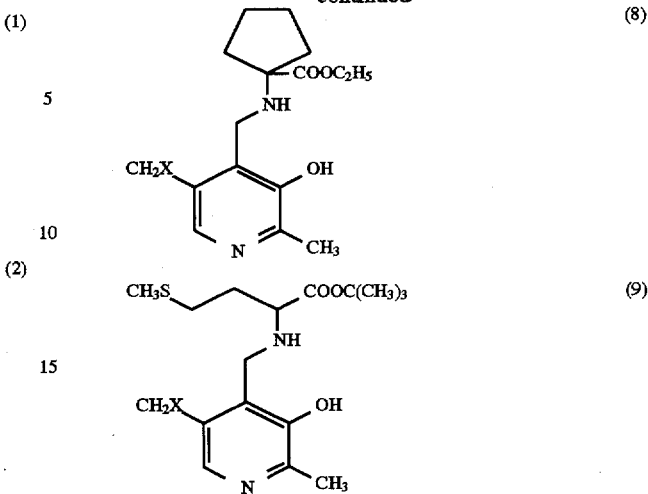

In the above formulae, X represents an —OH radical or a —OPO$_3$H$_2$ radical.

The compound corresponding to formula (9) wherein X represents an —OH radical is especially preferred.

Exemplary inhibitors of the transamidase involved in the transformation of 4-methylthio-2-oxobutanoic acid into methionine, and, thus, exemplary factors which increase the intracellular concentration of methional or malondialdehyde, are the hydroxamates of amidoamino acids, such as the hydroxamate of D-asparagine having the formula CONHOHCH$_2$CHNH$_2$COOH, and the hydroxamate of L-glutamine, having the formula CONHOHCH$_2$CH$_2$CHNH$_2$COOH.

When induction of apoptosis is desired, it is preferred to use a compound selected among methional, malondialdehyde, compounds which, in situ, release methional or malondialdehyde, e.g., esters or thioesters of methional or malondialdehyde, or activators of the enzyme involved in the transformation of methional or malondialdehyde.

Especially advantageous immixtures for triggering apoptosis include immixtures of methional with at least one inhibitor of the transaminase involved in the transformation of 4-methylthio-2-oxobutanoic acid into methionine, and preferably, the compounds corresponding to the above structural formula (9).

When the suppression of apoptosis is desired, it is preferred to use inhibitors of enzymes responsible for the production of methional or malondialdehyde, such as 2-oxobutyrate and/or activators of enzymes responsible for the elimination of methional, other than by means of the aforementioned β-hydroxylation reaction.

The compositions according to the invention are particularly suitable in the following fields of therapy:

(1) For treating dermatological conditions asssociated with keratinizalion disorders relating to differentiation and hyperproliferation, and in particular for treating common, blackhead and polymorphous acne, acne rosacea, nodulocystic and conglobate acne, senile acne, and secondary acne, such as solar, drug-related, and professional acne;

(2) For treating other types of keratinization disorders, such as ichthyosis, ichthyosiform conditions, Darier's disease, palmoplantar keratoderma, leukoplakia and leukoplakiform conditions, and cutaneous or mucosal (buccal) lichen;

(3) For treating other dermatological conditions associated with keratinization disorders manifesting an inflammatory and/or immunoallergic component, and, in particular, all forms of psoriasis, whether cutaneous, mucosal, or ungual, and even psoriatic rheumatism, or cutaneous atopy, such as eczema or respiratory atopy, or gingival hypertrophy;

(4) For treating dermal or epidermal hyperproliferatioms, whether benign or malignant and whether viral or non-viral in origin, such as common and flat warts and wart-shaped epidermodysplasia, oral or florid papillomatosis, hyperproliferations caused by ultraviolet exposure, in particular in baso- and spinocellular epithelioma;

(5) For treating other dermatological disorders, such as bullous dermatosis and collagen-related disorders;

(6) For treating certain ophthalmological conditions, in particular corneopathisis;

(7) For repairing or combating skin aging, whether photoinduced or chronologic, or to decrease pigmentation and actinic keratosis, or any pathology associated with chronological or actinic aging;

(8) For preventing or curing the signs of epidermal and/or dermal atrophy induced by local or systemic corticosteroids, or all other forms of cutaneous atrophy;

(9) For preventing or treating scarring or for preventing or repairing striae atrophicae;

(10) For combating sebaceous function disorders, such as acne-related or simple hyperseborrhea;

(11) For the treatment or prevention of cancerous or precancerous states;

(12) For the treatment of inflammatory conditions such as arthritis;

(13) For the treatment of all cutaneous or generalized conditions of viral origin, such as hepatitis;

(14) For the prevention or treatment of alopecia;

(15) For the treatment of dermatological or generalized dermatological conditions manifesting an immunological component;

(16) For the treatment of disorders of the cardiovascular system, such as arteriosclerosis and thrombocytopenia;

(17) For the treatment of neurodegenerative diseases, such as Alzheimer's.

For the aforesaid therapeutic or pharmaceutical applications, the compositions according to the invention may advantageously contain other active agents, such as retinoids, anti-free radical agents, vitamin D derivatives, corticosteroids or estrogens, antioxidants, α-hydroxy or α-keto acids and derivatives thereof, and ion channel blockers, e.g., potassium blockers.

The present invention thus also features cosmetic or pharmaceutical compositions suited to modulate apoptosis, especially for the preventive and/or curative treatments indicated above.

The retionoids intended for inclusion in the subject compositions may be natural or synthetic, including 9-cis retinoic acid and all-trans retinoic acid.

Among the vitamin D compounds or derivatives thereof, particularly representative are the derviatives of vitamin $D_2$ and $D_3$, and especially 1,25-dihydroxyvitamin $D_3$.

Among the anti-free radical agents thus intended are α-tocopherol, superoxide dismutase, Ubiquinol, or certain metal chelating agents.

The α-hydroxy or α-keto acids and derviatives thereof suited for inclusion includes ketoleucine, ketoisoleucine, ketovaline, 2-oxobutyrate, 4-methylthio-2-oxobutanoic acid, lactic, malic, citric, glycolic, mandelic, tartaric, glyceric, and ascorbic acid and derivatives of salicyclic acid and the salts, amides, and esters thereof.

The ion channel blockers include Minoxidil (2,4-diamine-6-piperidinopyrimidine-3-oxide) and derivatives thereof.

The compositons according to the invention may be administered systemically, enterally, parenterally, topically, or ocularly. The final product is preferably packaged such as to facilitate systemic administration, i.e., by injection or perfusion.

For enteral administration, the medicinal/pharmaceutical compositions may be in the form of tablets, gelatin capsules, sugar-coated tablets, pills, syrups, suspensions, solutions, elixirs, powders, granules, emulsions, microspheres, nanospheres, and lipid and polymeric vesicles permitting a controlled release. Parenterally, the subject compositions may be in the form of solutions or suspensions intended for perfusion or injection.

The compounds according to the invention are normally administered in one daily amount of approximately 0.001 to 100 mg/kg body weight, and this at the regime or rate of 1 to 3 doses per diem.

Topically, the compositions according to the invention are more especially intended for treatment of the skin and mucous membranes, and are provided as salves, creams, milks, ointments, powders, pommades, buffer solutions for oral administration, impregnated pads, gels, sprays, lotions, or suspensions. They may also be provided on the form of microspheres, nanospheres, or lipid or polymeric vesicles, or polymeric or hydrogel patches permitting controlled or precision release. These compositions administered topically may be in anhydrous or aqueous form.

For ocular administration, the subject compositions are principally on the form of eye lotions.

The pharmaceutical compositons administered topically or to the eye contain methional, malondialdehyde, or any factor influencing the intracellular concentration of methional or malondialdehyde, in an amount perferably ranging from 0.001% to 5% of the total weight of the composition.

The compositions according to the invention also find application in the field, in particular for body hygiene and hair care, and especially for the treatment of acne-stricken skin, and hair regeneration or regrowth and hair preservation, protection against the harmful effects of the sun and in the treatment of physiologically dry skin, to prevent and/or combat photoinduced or chronological aging.

Too, the present invention features a regimen for preventing and/or combating photoinduced or chronological skin aging, comprising topically applying a cosmetic composition triggering apoptosis as described above, to the skin.

For cosmetic applications, the compositions of the invention may advantageously contain retinoids, D vitamins or derivatives thereof, corticosteroids, anti-free radical agents, α-hydroxy- or α-keto acids or derivatives thereof, or ion channel blockers. These various active agents according to the present invention are those indicated above.

The cosmetic compositions according to the invention are advantageously in the form of a cream, a milk, a lotion, a gel, microspheres, nanospheres, or lipid or polymeric vesicles, soaps, or shampoos.

The concentration of the methional, malondialdehyde, or any factor influencing the intracellular concentration of methional or malondialdehyde in the cosmetic compositon perferably ranges from 0.0001% to 3% by weight relative to the total weight of the composition.

The pharmaceutical or cosmetic compositions according to the invention may, in addition, contain inert or even pharmacodynamically or cosmetically active additives or combinations of these additives, and, in particular: wetting agents; depigmentation agents such as hydroquinone, azelaic, caffeic, or kojic acid; emollients; hydrating agents such as glycerol, PEG 400, thiamorpholinone and its derivatives, and urea; antiseborrhea and antiacne agents, such as S-carboxymethylcysteine, S-benzylcysteamine and the salts and derivatives thereof, and benzoyl peroxide, antibiotics such as erythromycin and esters thereof, neomycin, clindamycin and esters thereof, and tetracycline; antifungal agents such as ketoconazole and 4,5-polymethylene-3-isothiazolinones; agents promoting hair restoration, such as Minoxidil (2,4-diamino-6-piperidine-pyrimidine-3-oxide) and derivatives thereof, Diazoxide (7-chloro-3-methyl-1,2,4-benzothiadiazine-1,1-dioxide) and Phenytoin (5,4-diphenylimidazolidine-2,4-diketone); non-steroidal anti-inflammatory agents; carotenoids and, in particular, β-caratone; anti-psoriatic agents such as anthralin and derivatives thereof, and lastly, 5,8,11,14-eicosatetraynoic and 5,8,11-eicosatrynoic acids and esters and amides thereof.

The compositions according to the invention may also contain taste- or flavor-enhancing agents, preservatives such as esters of parahydroxybenzoic acid, stabilizers, moisture-regulating agents, pH regulating agents, osmotic pressure-modifying agents, emulsifiers, UW-A and UV-B screens, and antioxidants such as α-tocopherol butylated hydroxyanisole and butylated hydroxytoluene.

In order to further illustrate the present invention and the advantages thereof, the following specific examples are given, it being understood that same are intended only as illustrative and in nowise limitative.

EXAMPLE 1

Effect of metabolites on the growth of HeLa cells:

HeLa cells ($0.5 \times 10^6$ per Petri dish) were cultured in 3 ml of a minimum essential Eagle medium containing 10% by weight dialyzed fetal calf serum. After four hours, methional (10 µM–1 mM), methionol (10 µM–20 mM), methylthiopropionic acid (MTPA) (1 µM–20 mM), L-methionine (1 µM–20 mM) or 4-methylthio-2-oxobutanoic acid (MTOB) (1 µM–20 mM) were added to each of the three dishes. After three days at 37° C., the cells were washed twice in a buffered, phosphatized saline medium having a pH of 7.5 (PBS medium) and collected in the same type of buffer.

Cell growth was assessed by measuring protein content (see technique described in O. H. Lowry, N. J. Rosebrouh, A. L. Farr, and R. J. Randall, *J. Biol. Chem.*, 193, 265–275 (1951)) or the DNA content in the lysate using a bisbenzimide trihydrochloride solution (Hoechst 33258) (see W. D. Jarvis, R. N. Kolesnick, F. A. Fornari, R. S. Traylor, D. A. Gewirtz, and S. Grant, *Proc. Natl. Acad. Sci. USA*, 91, 73–77 (1994)), or by determining lactic dehydrogenase activity using 3-(4,5-dimethylthiazol-2-yl)-2,5-diphenyl-tetrazolium bromide (MTT) (see T. Mosmann, *J. of Immunology, Methods*, 65, 55–63 (1983)).

The results obtained are reported in Table 1. Each value of is the average of 3 or 4 experiments as estimated by protein content.

TABLE 1

| Product | IC50 (mM) |
| --- | --- |
| L methionine | >20 |
| MTOB | 1.6 |
| methional | 0.10 |

TABLE 1-continued

| Product | IC50 (mM) |
| --- | --- |
| methionol | >20 |
| MTPA | 10 |

IC50 represents the concentration of compound required to inhibit cell growth by 50%.

The results assessed by measuring the DNA content or by determining lactic dehydrogenase activity were comparable to those reported in the above Table 1.

The table illustrates the difference between the IC50 for methional and the IC50s for the compounds or precursors thereof.

EXAMPLE 2

HeLa cells ($0.5 \times 10^6$ per Petri dish) were cultured in 3 ml of a minimum essential Eagle medium not containing methionine and containing 10% by weight dialyzed fetal calf serum. After four hours, 2-oxobutyrate (10 mM–40 mM) in the presence of 2 mM 4-methylthio-2-oxobutanoic acid (MTOB) were added. After three days at 37° C., the cells were washed twice in a buffered, phosphatized saline medium having a pH of 7.5 (PBS medium) and collected in the same type of buffer. Cell growth was measured in the same manner as in the preceding example.

2-oxobutyrate is a well-known substrate of the branched-chain oxoacid dehydogenase complex (BCOADC) (Km 18 µM). 2 mM MTOB alone caused a 72% inhibition of growth. The results indicated that 2-oxobutyrate had the ability to eliminate this inhibition of growth. Beginning at a level of 10 mM 2-oxobutyrate, inhibition decreased 2–3 times. Thus, it was found that BCOADC tending to transform the MTOB into methional was shifted toward a different substrate, e.g., 2-oxobutyrate, thereby reducing inhibition of growth.

EXAMPLE 3

Effect of methional on DNA fragmentation in BAF3 cells:

The cells used corresponded to BAF3 mouse lymphocytic cell line which required interleukin 3 (IL3) for growth, and which displayed apoptosis (in excess of 80% of the cells) in the absence of IL3 over 16 hours [see M. K. L. Collins, J. Marvel, P. Malde, and A. Lopez-Rivas, *J. Exp. Med.*, 176, 1043–1051 (1992)].

$3 \times 10^6$ BAF3 cells were grown in 6 ml of a culture medium containing IL3 in Petri dishes in the presence of different concentrations (200–800 µM) of methional or propanol, a substrate of the aldehyde dehydogenase. After 8 hours of contact, the cells were washed three times in a phosphatized buffered saline medium, pH=7.5 (PBS medium). These cells were lysed in 2 ml 0.1% Triton X-100, 20 mM EDTA (ethylenediaminetetraacetic acid), 5 mM Tris pH 8, and then centrifuged at 30,000 g at 4° C. for 30 minutes. The supernatants were decanted and analyzed as indicated below.

For purposes of comparison, the same cultures were grown in a medium, either with IL3 (+IL3) or without IL3 (−IL3).

The DNA fragments obtained were analyzed qualitatively using the method described, in particular, in W. D. Jarvis, R. N. Kolesnick, F. A. Fornari, R. S. Traylor, D. A. Gawiriz, and S. Grant, *Proc. Natl. Acad. Sci. USA*, 91, 73–77 (1994). The supernatants were treated with ribonuclease A (20 µg/ml) for 1 hour at 37° C., and with the proteinase R (100 µg/ml). The DNA was purified using phenol extraction and precipitated with ethanol.

In the final extract, the DNA fragments having low molecular weights were analyzed by 1% agarose gel electrophoresis. After electrophoresis (60V, 3 hours), the gels were stained with ethydium bromide.

The results clearly showed that apoptosis was triggered with the methional; the gel produced evidenced a ladder of multiple DNA fragments containing 180 to 200 base pairs typical of the triggering of apoptosis. When using propanol, the gel did not possess this characteristic.

Spectrofluorometric analysis was carried out to measure the quality of DNA fragments obtained (<3 kilobases). 1 ml of a solution of bisbenzimide trihydrochloride (Hoechst 33258) (1 µg/ml) in 3 mM sodium chloride, 1 mMd4EDTA, 10 mM Tris, pH=8, was added to 2 ml supernatant. The solutions obtained were analyzed by fluorometry (excitation λ=365 nm, emission λ=460 nm). The quantities of DNA were calculated in relation to highly-purified DNA (0.1 to 1 µh in 2 ml lysis buffer) treated as indicated above and expressed in $10^{-9}$ g DNA collected from $3 \times 10^6$ cells.

The results obtained are reported in Table 2 below:

TABLE 2

| Examples | $10^{-9}$ gDNA/$3 \times 10^6$ cells |
| --- | --- |
| +IL3 | 63 |
| +IL3 + Methional | 127 |
| −IL3 | 150 |

Thus, the increase in the amount of DNA fragments found in the cells treated with IL3 and methional was comparable to the quantity found when the cells were placed in a medium not containing IL3.

EXAMPLE 4

Effect of BCNU and an inhibitor of the transaminase implicated in transforming 4-methylthio-2-oxobutanoic acid into methionine on the production of reactive oxygenated substances ($H_2O_2$ and $HO^-$):

$1.5 \times 10^6$ BAF3 cells (cell line described above) seeded in 3 ml of a culture medium containing IL3 [Dulbecco-modified Eagle medium containing 6% fetal calf serum and 5% of a medium treated with Wehl-3B cells used in the IL3 source, a medium described in Collins et al, J. Exp. Med., 176, 1043–1061 (1992)] were treated with 10 µM of 2',7'-dichlorofluorescein-diacetate (hereinafter designated DCFH-DA, marketed by Molecular Probes Inc.). After an incubation time of one hour at 37° C., the cells were washed with a PBS buffer. 10 minutes before fluorescence analysis of dichlorofluorescein (DCF) by flow cytometry, 3 µg/ml propidium iodide were added. Incubation was carried out in the presence of various concentrations of BCNU and in the presence or absence of compound A in a concentration of 50 µM (which corresponded to the compound corresponding to formula (9) wherein X is a —OH radical). This technique provided the percentage of fluorescence obtained by reaction of the reactive oxygenated substrates ($H_2O_2$ and HO-) with DCFH-DA. Flow cytometry was conducted using a FACScan flow cytometer (Becton Dickinson, San Jose, Calif., USA).

The results obtained are reported in Table 3:

TABLE 3

| BCNU concentration (µg/ml) | compound A concentration (µM) | Fluorescence/ $10_6$ cells (%) |
| --- | --- | --- |
| 10 | 0 | 4 |
| 20 | 0 | 4 |
| 40 | 0 | 10 |
| 10 | 50 | 2.5 |
| 20 | 50 | 1.5 |
| 40 | 50 | 1.76 |

These results demonstrated that compound A, which made it possible to increase the methional content, suppressed the increase of $HO^-$ resulting from the increased concentration of BCNU. It was, accordingly, plausible that a reaction of methional with the $HO^-$ radicals present had occurred, thus providing the malondialdehyde which then triggered apoptosis.

EXAMPLE 5

Effect of BCNU and of an inhibitor of the transaminase implicated in the transformation of 4-methylthio-2-oxobutanoic acid into methionine on apoptosis:

The DNA strand cuttings were marked with biotinylated dUTP (detected by avidin fluorescein), in situ, in the cells rendered permeable and fixed using the terminal DNA transferase deoxynucleotidyl test (TdT), as described in Gorczyca et al, Cancer Res., 53, 1945–1951 (1993). $1.5 \times 10^6$ BAF3 cells (cell line described above) seeded in 3 ml of a culture medium containing IL3 (Dulbecco-modified Eagle medium containing 6% fetal calf serum and 5% of a medium treated with Wehl-3B cells used in the IL3 source). The cells were incubated in the presence of compound A in a concentration of 50 µM, 40 µg/ml of BCNU, and the mixture of these two compounds (50 µM of compound A+40 µg/ml of BCNU) or in the absence of these two compounds (control). After a 24-hour incubation period of time, the cells were washed in PBS buffer and fixed in formaldehyde, then in ethanol, and maintained a −20° C. for 3 days. Next, the cells were again placed in suspension in 50 µl of a solution containing 0.1 µM sodium cacodylate, pH=7.5, 1 mM $CoCl_2$, 0.1 mM dithiothreitol, 0.05 mg/ml Bovine Serum Albumin, 10 units TdT (from Boerhringer calf thymus), 0.5 nmol dCTP, and 0.5 nmol dGTP for one hour at 37° C. After washing in PBS, the cells were again placed in suspension in 100 µl 4xSSC buffer (0.15M NaCl, 0.015M sodium citrate) containing 25 µg/ml avidin-fluorescein isothiocyanate (Sigma), 0.1% (weight/vol.) of RNAase A, 0.1% Triton X100, and 5% (weight/vol.) nonfat milk for 30 minutes at ambient temperature under dark conditions. These cells were washed, then placed in suspension in 1 ml PBS containig 3 µm/ml propidium iodide. Flow cytometry was carried out using a FACScan flow cytometer (Becton Dickinson, San Jose, Calif., USA).

The results obtained are reported in Table 4:

TABLE 4

| Test | % apoptotic cells |
| --- | --- |
| control | 0.2 |
| Compound A | 0.3 |
| BCNU | 2.3 |
| Compound A + BCNU | 41.1 |

In these quantities, the products by themselves weakly triggered apoptosis. On the other hand, the mixture thereof strongly induced apoptosis (synergy). This result confirmed the results reported in Table 3 and the conclusions reached therefrom.

EXAMPLE 6

Determination of the most effective theraputic combination for treating mice into which melanoma cells had been grafted:

At t=0 day, $10^5$ murine B16 Fl melanoma cells were injected into B6D2F1 mice (from the IFFA CREDO Company, France). At t=day and continuuly for 15 days, different theraputic regimens as indicated in Table 5 below, were injected once daily into these mice. The control included mice which did not receive any therapeutic regimen.

Table 5 reports the results corresponding to averages of the results obtained on three treated mice.

TABLE 5

| Therapuetic Regimen (mg/kg) | Average Survival Time (days) |
|---|---|
| Control | 20.5 |
| BCNU (0.1 mg/kg) | 24.5 |
| Compound A (25 mg/kg) | 21.9 |
| Methional (25 mg/kg) | 27 |
| BCNU + Methional | 26 |
| Compound + Methional | 27 |
| BCNU + Compound A | 40.6 |
| BCNU + Compound A + Methional | 57 |

For the regimens containing multiple compounds, the quantities of each of the compounds used were identical to those of the regimens using the compounds by themselves.

Survival time was recorded beginning at t=0 day, as indicated above.

BCNU corresponds to N,N-Bis(2-chloroethyl)-N-nitrosourea. Compound A corresponds to the compound having formula (9), wherein X is a —OH radical.

It can thus be seen that the two latter regimens were especially effective, since they increased significantly the survival time of the mice. Between the two regimens, the latter (to which methional was added) accounted for one-third of the mice surviving more than 60 days. The "average survival time" is the mean of the number of mice dying over the course of the experiment, i.e., within 60 days.

EXAMPLE 7

The procedure of the previous example was repeated, but the regimens and numbers of mice treated varied. Table 6 reports these data and the results obtained:

TABLE 6

| Therapeutic Regimen (mg/kg) | No. of mice treated | Average survival time (days) | % long-term survivors |
|---|---|---|---|
| control | 6 | 23.7 | 0 |
| BCNU (0.1 mg/kg) | 6 | 32.5 | 0 |
| Compound A (25 mg/kg) + Methional (50 mg/kg) | 10 | 33.1 | 10 |
| BCNU + Compound A + Methional | 10 | 36 | 50 |

With respect to this latter regiment, the quantities corresponded to the quantities of compounds used alone. The percentage of long-term survivors corresponded to the percentage of mice which survived beyond 60 days.

It will thus be seen that the two latter regimens, and especially the last one, were especially effective.

EXAMPLE 8

Effect of methional on the induction of apoptosis in BAF3-bO and BAF3-bcl2 cells:

The cells used were a BAF3 lymphocytic cell line, such as that described above. The BAF3-bcl2 cells corresponded to BAF3 cells transfected by the bcl2 gene. The BAF3-bO cells corresponded to BAF3 cells not transfected by the bcl2 gene. As indicated above, the BAF3-bO cells underwent apoptosis (more than 80% of the cells) in the absence of IL3 for 16 hours. On the other hand, the BAF3-bcl2 cells, which were transfected by the bcl2 gene, evidenced no sign of apoptosis in the absence of IL3. Accordingly, they constituted a good model for determining the apoptosis step blocked in these cells, and its potential correlation with the inhibition of malondialdehyde synthesis.

The BAF3-bO or BAF3-bcl2 cells were marked by adaptation of the method described in S. Wright et al, *J. of Cell. Biochem.*, 48, 344–355 (1992), by incubating $2.5 \times 10^5$ cells/ml with 0.5 µCi [3H]-thymidine for 40 hours at 37° C. After two washings in a culture medium, $2.5 \times 10^6$ cells were cultured in the presence of methional. After incubation for 8 hours, these cells were collected by centrifugation at 400 g for five minutes and washed three times in PBS buffer. The cells collected in the residue were lysed in 2 ml of 0.1% Triton X100, 20 mM EDTA, 5 mM Tris, pH=8, and centrifuged at 30,000 g at 4° C. for 30 minutes. The supernatants were collected and the sediments dissolved in 0.3 ml of 0.5N NaOH. The aliquots of the culture medium (1 ml), of the supernatant (0.3 ml), and of the solubilized sediment (0.1 ml) were measured by quantitative analysis in the scintillation counter. The percentage of DNA fragments was calculated in the following manner:

% of DNA fragments=dpm of the culture medium+dpm of the supernatant dpm of culture medium+dpm of supernatant+dpm of solubilized sediment Results: the addition of an increasing concentration of methional (0; 50; 100; 200; 300; 400 µM) to the incubation medium increased the percentage of DNA fragments up to a maximum, at a concentration of 400 µM methional, of 26% as compared to 7% for BAF3 cells untreated with methional (control). When using BAF3-bcl2 cells treated with equivalent methional concentrations, the DNA fragments attained a maximum of 7% at a methional concentration of 400 µM, as compared with 3% for the control.

These results clearly evidenced that the addition of methional did not permit eliminating the inhibition of apoptosis resulting from the bcl2 gene in BAF3-bcl2 cells.

When apoptosis was induced by virtue of a lack of IL3, it was observed that the methional was transformed into malondialdehyde via a β-hydroxylation reaction using $HO^-$. Quantitative analysis of $H_2O_2$ and $HO^-$ was conducted in the BAF3-bO and BAF3-bcl2 cells.

EXAMPLE 9

Measurement of the reactive oxygenated substrates ($H_2O_2$ and $OH^-$) via the flow cytometry technique:

The cells used corresponded to a BAF3 lymphocytic cell line, as described above. The BAF3-bcl2 cells corresponded to BAF3 cells transfected by the bcl2 gene, and the BAF3-bO cells corresponded to BAF3 cells not transfected by the bcl2 gene.

$1.6 \times 10^6$ BAF3-bO or BAF3-bcl2 cells, seeded in 3 ml of a culture medium containing IL3, were treated with 10 µM dichlorofluorescein-diacetate (DCFH-DA). After incubation for one hour at 37° C., the cells were washed in a PBS buffer. 10 minutes prior to fluorescence analysis of the dichlorofluorescein (DCF) using flow cylometry, 3 µg/ml of propidium iodide were added, as in Example 4. Flow cytometry was carried out using a FACScan flow cytometer (Becton Dickinson, San Jose, Calif., USA).

The results obtained are reported in Table 7, below:

TABLE 7

| Cell Type | Average arbitrary fluorescence unit |
|---|---|
| BAF3-bO | 154 +/− 32 |
| BAF3-bcl2 | 211 +/− 52 |

In consequence, even though the BAF3-bcl2 cells tender to contain more reactive oxygenated substances than did the BAF3-bO cells, this difference was not significant.

It was possible, therefore, that the BAF3-bcl2 cells exhibited defective synthesis of methional and/or malondialdehyde.

EXAMPLE 10

Analysis of substrates marked with $^{14}C$ derived from [$^{14}C$] MTOB in BAF3-bO and BAF3-bcl2 cells:

The cells used were identical to those in the preceding example.

[$^{14}C$]MTOB was prepared by oxidative deamination of [$^{14}C$]Methionine, as described in Ogier et al, *Biochem. Pharmacol.*, 45, 1631–1644 (1993). [$^{14}C$]MTOB ($5 \times 10^6$ dpm corresponding to 38.2 nmol) was added to a cellular BAF3-bO or BAF3-bcl2 suspension ($2.4 \times 10^5$ cells/ml) in DMEM containing 6% fetal calf serum and 5% IL3. 39 hours later, the cells were washed twice in PBS and placed in suspension at a concentration of $9 \times 10^5$ cells/ml. [U $^{14}C$]MTOB ($1.9 \times 10^6$ dpm corresponding to 14.5 nmol) was added to $10^8$ cells, and, eight hours later, the cells were collected by centrifugation at 400 g for five minutes. The cellular sediments were solubilized using 1.5 ml of 0.5N NaOh for 30 minutes at 60° C. The total radioactivity in the cells was measured on 10 µl aliquots. Next, perchloric acid in a final concentration of 0.5N, then 200 µmol of 2,4-DNPH (2,4-dinitrophenylhyrazine, marketed by Merck) were added to the alkaline hydrolyzate obtained. The mixture was heated to 70° C. for 30 minutes, then centrifuged at 400 g for five minutes. The precipitate was solubilized ion 1 ml of 0.5N NaOH, and the radioactivity and protein content were determined. NaOH, pH=10, was added to the supernatant. The marked metabolites were extracted in ethylene acetate, and the organic phase was dried, acidified, and extracted in dichloromethane. The marked metabolites in the organic phase were separated out and identified using high-performance thin-layer chromatography and compared to the 2,4-DNPH derivatives of the reference compounds, then quantified by radiochromatography.

The results obtained are reported in Table 8, below:

TABLE 8

| | BAF3-bO | BAF3-bcl2 |
|---|---|---|
| Total radioactivity/mg of DNA | 1,252,000 | 1,111,000 |
| Spec. activity of cellular proteins (dpm/mg protein) | 23,500 | 20,850 |
| Free methional (dpm/mg of DNA) | 36,820 | 51,440 |
| 2,4-DNPH methional (dpm/mg of DNA) | 14,050 | 7,650 |
| 2,4-DNPH malondialdehyde (2,4-DNPH pyrazole) (dpm/mg of DNA) | 800 | 0 |

Thus, it was observed that total radioactivity as calculated for an identical quantity of DNA was similar in both cell types after incubation for 47 hours. The same was true as regards the activity of cellular protein methionine. As regards free metmonine, a 40% increase in radioactivity was observed in BAF3-bcl2 cells as compared with the quantity in BAF3-bO cells. The radioactivity in the methional was 80% higher in the BAF3-bO cells than in the BAF3-bcl2 cells. This observation evidenced that, in the BAF3-bcl2 cells, the decreased methional formation from MTOB was accompanied by a concomitant increase in methionine formation. When marked malondialdehyde formation was measured, it corresponded to 800 dpm/mg of DNA in the BAF3-bO cells, while no radioactivity with respect to the malondialdehyde was detected in the BAF3-bcl2 cell extracts. The BAF3-bcl2 cells thus also exhibited decreased malondialdehyde formation from methional. Example 8 clearly demonstrates that this decrease was not the result of a decrease of the reactive oxygenated species in the BAF3-bcl2 cells as compared with the BAF3-bO cells. It may this be concluded that, in addition to decreasing the transformation of MTOB into methional, the bcl2 gene negatively affects the β-hydroxylation reaction, which transforms methional into malondialdehyde.

Thus, all species which modulate the intracellular concentration of methional or metabolite thereof, or of malondialdehyde, are considered modulators of apoptosis.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A regimen for modulating apoptosis in a mammalian organism in need of such treatment, comprising administering to such organism, for such period of time as is required to elicit the desired response, an effective apoptosis-modulating amount of at least one active species selected from among methional, malondialdehyde, or factor influencing mammalian intracellular concentration of methional or malondialdehyde.

2. The regimen as defined by claim 1, comprising the suppression or inhibition of apoptosis.

3. The regimen as defined by claim 1, comprising the initiation or triggering of apoptosis.

4. The regimen as defined by claim 1, comprising administering to such organism at least one inhibitor of an enzyme responsible for the metabolism of methional and/or malodialdehyde.

5. The regimen as defined by claim 1, comprising administering to such organism at least one activator of an enzyme responsible for the metabolism of methional and/or malodialdehyde.

6. The regimen as defined by claim 1, comprising administering to such organism at least one intracellular metabolite of methional.

7. The regimen as defined by claim 6, comprising administering to such organism 4-methylthio-2-oxobutanoic acid, methionine, methionol, methylthiopropionic acid and/or methylthiopropionylCoA.

8. The regimen as defined by claim 1, comprising administering to such organism at least one prodrug of methional, malodialdehyde, or factor influencing the intracellular concentration thereof.

9. The regimen as defined by claim 8, comprising administering to such organism at least one ester or thioester of methional and/or malodialdehyde.

10. The regimen as defined by claim 1, comprising administering to such organism at least one inhibitor of an enzyme contributing to a metabolic methional-elimination reaction other than a β-hydroxylation reaction.

11. The regimen as defined by claim 1, comprising administering to such organism at least one activator of β-hydroxylase.

12. The regimen as defined by claim 10, comprising administering to such organism at least one inhibitor of a transaminase.

13. The regimen as defined by claim 1, comprising administering to such organism at least one active species that increases the intracellular concentration of OH⁻ free radicals.

14. The regimen as defined by claim 12, comprising administering to such organism at least one inhibitor of a transaminase contributing to the conversion of 4-methylthio-2-oxobutanoic acid into methionine.

15. The regimen as defined by claim 1, comprising administering to such organism at least one inhibitor or activator of the branched-chain oxoacid dehydrogenase complex contributing to the conversion of 4-methylthio-2-oxobutanoic acid into methylthiopropionylCoA.

16. The regimen as defined by claim 1, comprising administering to such organism at least one inhibitor or activator of a transaminase contributing to the conversion of 4-methylthio-2-oxobutanoic acid into methionine.

17. The regimen as defined by claim 1, comprising administering to such organism at least one inhibitor or activator of an aldehyde reductase contributing to the reduction of methional into methionol.

18. The regimen as defined by claim 1, comprising administering to such organism at least one inhibitor or activator of an aldehyde dehydrogenase contributing to the oxidation of methional into methylthiopropionic acid.

19. The regimen as defined by claim 1, comprising administering to such organism at least one inhibitor or activator of a β-hydroxylase contributing to the conversion of methional into malondialdehyde.

20. The regimen as defined by claim 16, comprising administering to such organism at least one compound having the structural formulae (1) to (9):

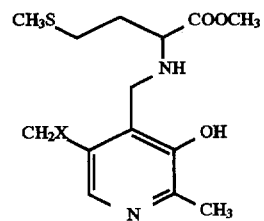
(1)

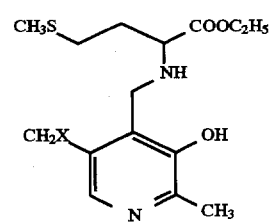
(2)

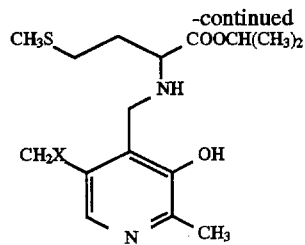
(3)

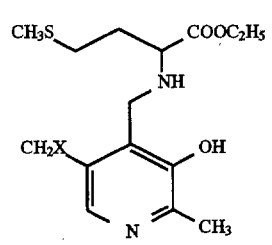
(4)

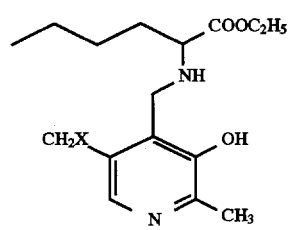
(5)

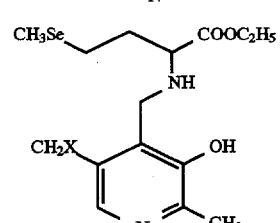
(6)

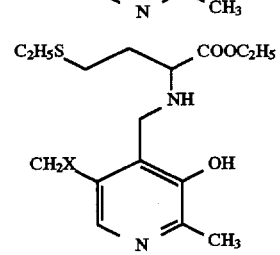
(7)

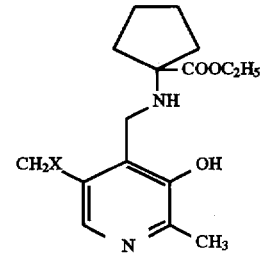
(8)

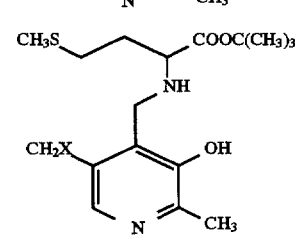
(9)

wherein X represents an —OH radical or —OPO₃H radical.

21. The regimen as defined by claim 16, comprising administering to such organism at least one hydroxamate of an amidoamino acid.

22. The regimen as defined by claim 1, comprising the treatment of breast cancer, B cell lymphoma, leukemia, neuroblastoma, adenocarcinoma of the prostrate, prolactinoma, or pituitary adenoma.

23. The regimen as defined by claim 1, comprising the prevention or treatment of photoinduced or chronologic skin aging.

24. The regimen as defined by claim 1, comprising coadministering to such organism a therapeutically effective amount of at least one retionoid, anti-free radical agent, vitamin D or derivative thereof, corticosteroid, estrogen, antioxidant, α-hydroxy or α-keto acid or derivative thereof, ion channel blocker, or combination thereof.

25. A pharmaceutical composition of matter, comprising an effective apoptosis-modulating amount of at least one active species selected from among methional, malondialdehyde, or factor influencing mammalian intracellular concentration of methional or malondialdehyde, in a pharmaceutically acceptable vehicle, diluent or carrier therefor.

26. The pharmaceutical composition as defined by claim 25, comprising an apoptosis-suppressing or apoptosis-inhibiting amount of said at least one active species.

27. The pharmaceutical composition as defined by claim 25, comprising an apoptosis-initiating amount of said at least one active species.

28. The pharmaceutical composition as defined by claim 25, comprising at least one inhibitor of an enzyme responsible for the metabolism of methional and/or malodialdehyde.

29. The pharmaceutical composition as defined by claim 25, comprising at least one activator of an enzyme responsible for the metabolism of methional and/or malodialdehyde.

30. The pharmaceutical composition as defined by claim 25, comprising at least one intracellular metabolite of methional.

31. The pharmaceutical composition as defined by claim 25, comprising 4-methylthio-2-oxobutanoic acid, methionine, methionol, methylthiopropionic acid and/or methylthiopropionylCoA.

32. The pharmaceutical composition as defined by claim 25, comprising at least one prodrug of methional, malodialdehyde, or factor influencing the intracellular concentration thereof.

33. The pharmaceutical composition as defined by claim 25, comprising at least one ester or thioester of methional and/or malodialdehyde.

34. The pharmaceutical composition as defined by claim 25, comprising at least one inhibitor of an enzyme contributing to a metabolic methional-elimination reaction other than a β-hydroxylation reaction.

35. The pharmaceutical composition as defined by claim 25, comprising at least one activator of β-hydroxylase.

36. The pharmaceutical composition as defined by claim 25, comprising at least one inhibitor of a transaminase.

37. The pharmaceutical composition as defined by claim 25, comprising at least one active species that increases the intracellular concentration of OH⁻ free radicals.

38. The pharmaceutical composition as defined by claim 25, comprising at least one inhibitor of a transaminase contributing to the conversion of 4-methylthio-2-oxobutanoic acid into methionine.

39. The pharmaceutical composition as defined by claim 25, comprising at least one inhibitor or activator of the branched-chain oxoacid dehydrogenase complex contributing to the conversion of 4-methylthio-2-oxobutanoic acid into methylthiopropionylCoA.

40. The pharmaceutical composition as defined by claim 25, comprising at least one inhibitor or activator of a transaminase contributing to the conversion of 4-methylthio-2-oxobutanoic acid into methionine.

41. The pharmaceutical composition as defined by claim 25, comprising at least one inhibitor or activator of an aldehyde reductase contributing to the reduction of methional into methionol.

42. The pharmaceutical composition as defined by claim 25, comprising at least one inhibitor or activator of an aldehyde dehydrogenase contributing to the oxidation of methional into methylthiopropionic acid.

43. The pharmaceutical composition as defined by claim 25, comprising at least one inhibitor or activator of a β-hydroxylase contributing to the conversion of methional into malondialdehyde.

44. The pharmaceutical composition as defined by claim 25, comprising at least one compound having the structural formulae (1) to (9):

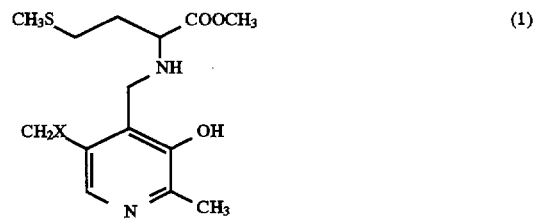

(1)

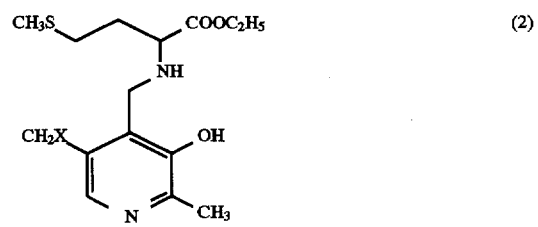

(2)

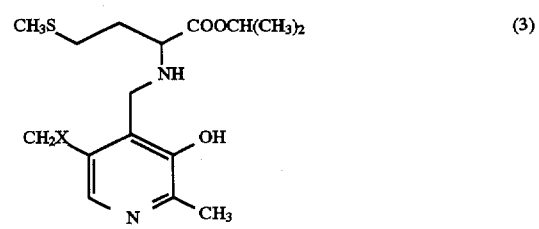

(3)

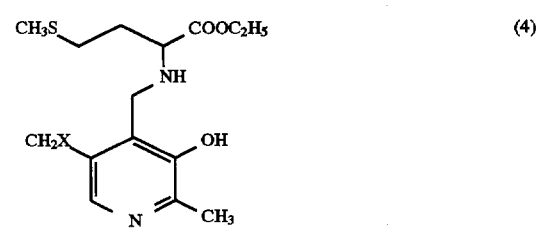

(4)

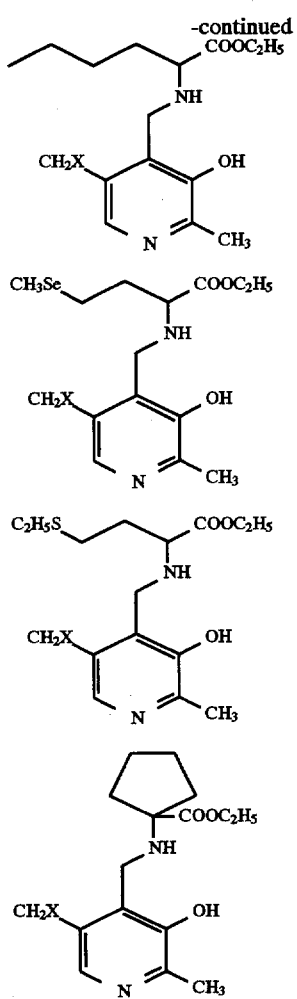

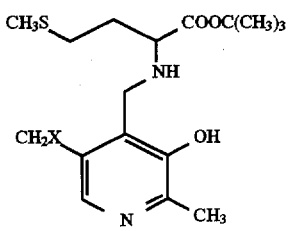

wherein X represents an —OH radical or —OPO$_3$H radical.

45. The pharmaceutical composition as defined by claim 25, comprising at least one hydroxamate of an amidoamino acid.

46. The pharmaceutical composition as defined by claim 25, adopted for systemic administration.

47. The pharmaceutical composition as defined by claim 25, adopted for topical administration.

48. The pharmaceutical composition as defined by claim 25, comprising from 0.001% to 5% by weight of said at least one active species.

* * * * *

UNITED STATES PATENT AND TRADEMARK OFFICE
CERTIFICATE OF CORRECTION

PATENT NO. : 5,744,499
DATED : April 28, 1998
INVENTOR(S) : Gerard Anthony Quash et al.

It is certified that error appears in the above-identified patent and that said Letters Patent is hereby corrected as shown below:

At Column 15, Table 8, line 58, please change "Free methional" to --Free methionine--.

At Column 15, line 67, please change "free methional" to --free methionine--.

At Column 9, line 20, please change "eicosatrynoic" to --eicosatriynoic--.

At Column 13, Table 5, line 26, please delete "Compound" and insert --Compound A--.

At Column 13, line 62, please delete "regiment" and insert --regimen--.

At Column 15, line 12, please change "tender" to --tend--.

At Column 16, line 12, please delete "example 8" and insert --Table 7--.

At Column 16, line 14, please delete "this" and insert --thus--.

Signed and Sealed this

First Day of June, 1999

Attest:

Attesting Officer

Q. TODD DICKINSON

Acting Commissioner of Patents and Trademarks